United States Patent [19]

Patil et al.

[11] Patent Number: 4,935,422
[45] Date of Patent: Jun. 19, 1990

[54] ACYLOXYPROPANOLAMINES

[75] Inventors: Ghanshyam Patil, Vernon Hills, Ill.; Khuong H. X. Mai, Chatworth, Calif.

[73] Assignee: E. I. Du Pont de Nemours and Company, Wilmington, Del.

[21] Appl. No.: 285,008

[22] Filed: Dec. 15, 1988

[51] Int. Cl.$^5$ .................. C07D 295/14; C07D 211/06; A61K 31/445; A61K 31/495
[52] U.S. Cl. ........................ 514/237.5; 514/255; 514/330; 514/423; 544/169; 544/390; 546/226; 548/538
[58] Field of Search ............ 514/237.5, 255, 330, 514/423; 544/169, 390; 546/226; 548/538

[56] References Cited

U.S. PATENT DOCUMENTS 4,692,446   9/1987   Erhardt et al. .................. 544/169

FOREIGN PATENT DOCUMENTS 8301770   5/1983   PCT Int'l Appl. .................. 544/169
8301772   5/1983   PCT Int'l Appl. .................. 544/169

Primary Examiner—Mary C. Lee
Assistant Examiner—MarySue Howard

[57] ABSTRACT

Compounds of the present invention, are represented by the general formula

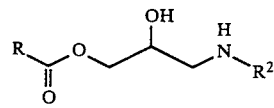

wherein R represents a straight or branched loweralkyl from 1 to about 6 carbon atoms, loweralkene from 2 to about 6 carbon atoms, or

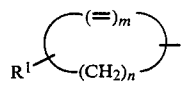

where m is o or 1 and n is 2, 3, 4, or 5 provided that when m is o, n is 2, 3, 4, or 5 and when m is 1, n is 3 or 4, and $R_1$ is hydrogen, a straight, branched or cyclic loweralky from 1 to about 6 carbon atoms or loweralkoxy, phenyl or substituted phenyl, and $R_2$ represents a straight or branched loweralkyl from 1 to about 6 carbon atoms or W-B wherein W represents alkylene of from 1 to about 10 carbon atoms which may be substituted with loweralkyl of from 1 to about 4 carbon atoms; and B represents hydrogen, —NHCOR$_4$, or —NHCONR$_3$R$_4$, wherein $R_3$ and $R_4$ may be the same or diffrent and may be hydrogen, alkyl, alkoxyalkyl, cycloalkyl, alkenyl, alkynyl, phenyl or aralkyl wherein the alkyl group contains from 1 to about 6 carbon atoms and the aryl group represents phenyl which may be unsubstituted or substituted with lower alkyl from 1 to about 6 carbon atoms, alkoxy wherein the alkyl group contains from 1 to about 6 carbon atoms, halogen, acetamido, amino, hydroxy, hydroxyalkyl of from 1 to about 10 carbon atoms; thiophenyl, imidazole, oxazole or indole, furanyl, tetrahydrofuranyl or $R_3$ and $R_4$ may together with N form a pyrrolidino, piperidino, piperazino, or morpholino ring, or a pharmaceutically acceptable salt thereof. The compounds are useful in the treatment or prophylaxis of cardiac disorder or in the treatment of glaucoma.

13 Claims, No Drawings

ACYLOXYPROPANOLAMINES

BACKGROUND OF THE INVENTION

Compounds of the present invention are useful because of their valuable pharmaceutical properties. They exhibit β-adrenergic blocking activity and are also useful in the treatment of glaucoma.

The present invention also relates to the treatment or prophylaxis of cardiac disorders. More particularly, the invention relates to a novel method of treatment or prophylaxis of cardiac disorders which comprises administration of β-adrenergic blocking agents and to compounds useful in such methods.

The therapeutic and prophylactic uses of compounds which block sympathetic nervous stimulation of β-adrenergic receptors in the heart, lungs, vascular system and other organs are well documented. Typically, such compounds are administered therapeutically to patients suffering from ischemic heart disease or myocardial infarction for the purpose of reducing heart work, i.e., heart rate and contractile force. Reducing heart work reduces oxygen demand, and may also actually increase oxygen supply. Thus, reducing heart work can aid in the prevention of further tissue damage and can relieve angina pectoris.

β-adrenergic stimulation may also aggravate or cause arrhythmias because of increased levels of catecholamines. Thus, β-blocking agents may be employed to reduce the risks of arrhythmias.

SUMMARY OF THE INVENTION

Compounds of the present invention, are represented by the general formula

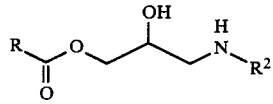

wherein R represents a straight or branched loweralkyl from 1 to about 6 carbon atoms, loweralkene from 2 to about 6 carbon atoms, or

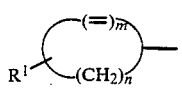

where m is o or 1 and n is 2, 3, 4, or 5 provided that when m is o, n is 2, 3, 4, or 5 and when m is 1, n is 3 or 4, and $R_1$ is hydrogen, a straight, branched or cyclic loweralkyl from 1 to about 6 carbon atoms or loweralkoxy, phenyl or substituted phenyl, and $R_2$ represents a straight or branched loweralkyl from 1 to about 6 carbon atoms or W-B wherein W represents alkylene of from 1 to about 10 carbon atoms which may be substituted with loweralkyl of from 1 to about 4 carbon atoms; and B represents hydrogen, —NHCOR$_4$, or —NHCONR$_3$R$_4$, wherein $R_3$ and $R_4$ may be the same or different and may be hydrogen, alkyl, alkoxyalkyl, cycloalkyl, alkenyl, alkynyl, phenyl or aralkyl wherein the alkyl group contains from 1 to about 6 carbon atoms and the aryl group represents phenyl which may be unsubstituted or substituted with lower alkyl from 1 to about 6 carbon atoms, alkoxy wherein the alkyl group contains from 1 to about 6 carbon atoms, halogen, acetamido, amino, hydroxy, hydroxyalkyl of from 1 to about 10 carbon atoms; thiophenyl, imidazole, oxazole or indole, furanyl, tetrahydrofuranyl or $R_3$ or $R_4$ may together with N form a pyrrolidino, piperidino, piperazino, or morpholino ring, or a pharmaceutically acceptable salt thereof. The compounds are useful in the treatment or prophylaxis of cardiac disorders or in the treatment of glaucoma.

DETAILED DESCRIPTION OF THE INVENTION

In accordance with the present invention, disclosed herein are compounds of the general formula

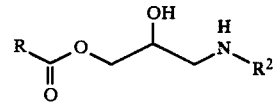

wherein R represents a straight or branched loweralkyl from 1 to about 6 carbon atoms, loweralkene from 2 to about 6 carbon atoms, or

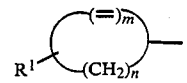

where m is o or 1 and n is 2, 3, 4, or 5 provided that when m is o, n is 2, 3, 4, or 5 and when m is 1, n is 3 or 4, and $R_1$ is hydrogen, a straight, branched or cyclic loweralkyl from 1 to about 6 carbon atoms or loweralkoxy, phenyl or substituted phenyl, and $R_2$ represents a straight or branched loweralkyl from 1 to about 6 carbon atoms or W-B wherein W represents alkylene of from 1 to about 10 carbon atoms which may be substituted with loweralkyl of from 1 to about 4 carbon atoms; and B represents hydrogen, —NHCOR$_4$, or —NHCONR$_3$R$_4$, wherein $R_3$ and $R_4$ may be the same or different and may be hydrogen, alkyl, alkoxyalkyl, cycloalkyl, alkenyl, alkynyl, phenyl or aralkyl wherein the alkyl group contains from 1 to about 6 carbon atoms and the aryl group represents phenyl which may be unsubstituted or substituted with lower alkyl from 1 to about 6 carbon atoms, alkoxy wherein the alkyl group contains from 1 to about 6 carbon atoms, halogen, acetamido, amino, hydroxy, hydroxyalkyl of from 1 to about 10 carbon atoms; thiophenyl, imidazole, oxazole or indole, furanyl, tetrahydrofuranyl or $R_3$ and $R_4$ may together with N form a pyrrolidino, piperidino, piperazino, or morpholino ring, or a pharmaceutically acceptable salt thereof. The compounds are useful in the treatment or prophylaxis of cardiac disorder or in the treatment of glaucoma.

Some of the compounds of the present invention selectively block β-adrenergic receptors in various organs. β-receptors in the heart are generally referred to as $β_1$ receptors, and those associated with vasodilation and bronchodilation are $β_2$ receptors. Selective β-blockers are preferred for the treatment of cardiac disorders, because they may have less potential to cause hypertension or bronchoconstriction. A number of $β_1$ selective adrenergic blocking agents have been discovered [Smith, L. H., *J. Appl. Chem. Biotechnol.*, 28, 201–202 (1978)]. Most compounds are structural variations of 1-amino-3-aryloxy-2-propanol.

Compounds of the present invention are also useful for the treatment of glaucoma or lowering of intraocular pressure by topical administration of the compounds to the eye.

The present compounds may be administered to warm-blooded animals orally or parenterally. They can generally be administered with a pharmaceutical carrier. The term "pharmaceutical carrier", for the purpose of the present invention, is intended to refer to any medium that is suitable for the preparation of a dosage unit form, and, thus, includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For parenteral administration, amounts of from about 0.001 to about 100 mg/kg per patient, per hour, are useful, with the total dose of up to 0.2 to 2 grams per day being a suitable range for large animals, including humans. A preferred dosage range is from about 0.01 to about 10 mg/kg of body weight per hour. Suitable intravenous dosage forms are sterile solutions of the compounds of the present invention or a pharmaceutically acceptable salt thereof, containing between about 0.05% and 2% w/v of active compound. When the compounds of the invention are to be used for the treatment of cardiac disorders such as, for example, angina pectoris or cardiac arrhythmias, or for the treatment of hypertension; it is expected they would be administered at a total oral dose of about 25 mg to 1200 mg daily. Suitable oral dosage forms are tablets or capsules containing between about 25 mg to 200 mg of active compound.

For all dosage forms the above exemplified compounds can be placed in capsules, formulated into pills, wafers, or tablets in conventional fashion together with pharmaceutical carriers well known in the art. Tablets may be perpared for immediate release of the active compound or they may be made enteric, i.e., whereby the active ingredient is released slowly over a period of several hours from within the intestinal tract.

In order to illustrate the manner in which the above compounds may be prepared and the properties of the compounds, reference is made to the following examples, which, however, are not meant to limit or restrict the scope of the invention in any respect.

In the following examples, melting points were obtained on a Thomas-Hoover melting point apparatus and are uncorrected.

A typical procedure for the synthesis of compounds 5-9.

for one hour, washed with water, 5% HCl, 5% NaHCO₃, brine, dried over MgSO₄, filtered and evaporated under reduced pressure to an oil (13 g, 91%). NMR and IR data are consistent with the assigned structure. This crude product is pure enough to be used in the next step without any further purification.

Using the corresponding alkyl and cycloalkyl carboxylic acid chlorides, instead of cyclopropyl carboxylic acid chloride in the above procedure, the following epoxide derivatives can be made.

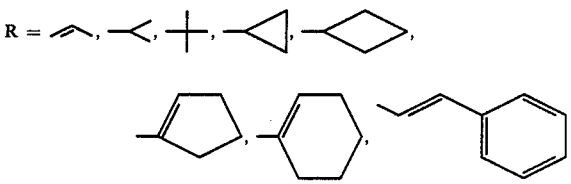

Preparation of Compound 15

To an ice-cooled solution of 1,2-diamino-2-methylpropane (88.16 g, 1 mole, from Aldrich Chemical Company) in ether (300 ml) was added slowly, drop wise isobutyric anhydride. Stirred for 1 hour at 0° C. and the reaction mixture was filtered. The filtrate was evaporated under reduced pressure to a clear oil. This oil was pumped at 75° C. under high vacuum (to remove excess diamine) (36 g, 91%). Used as it is in the next step.

Preparation of Compound 6 (R=cyclopropyl)

A mixture of glycidol cyclopropyl carboxylate 14 (7 g, 0.05 mole), 1,1-dimethyl-2-[isopropylcarboxamido]ethylamine (5 g, 0.03 mole) and DMF (30 mL) was stirred and heated at 60° C. for 6 hours. The reaction mixture was concentrated under reduced pressure and the residue was taken up in ethylacetate (20 mL) and filtered. The filtrate was acidified with a solution of oxalic acid in ethylacetate. Immediately a turbid solution was obtained. This was filtered off and the filtrate was evaporated under reduced pressure. The residue triturated with acetone (10 mL) to give crystalline solid. MEK (10 mL) was added and the product was isolated by filtration and dried under vacuum (0.2 g) m.p. 102° to 105° C.

Elemental Analysis: $C_{15}H_{28}N_2O_4 \cdot C_2H_2O_4 \cdot H_2O$ Cal. % C, 50.00; % H, 7.89; % N, 6.86. Found. % C, 50.34; % H, 7.49; % N, 6.91.

Compound 12 pk can be synthesized by the same pro-

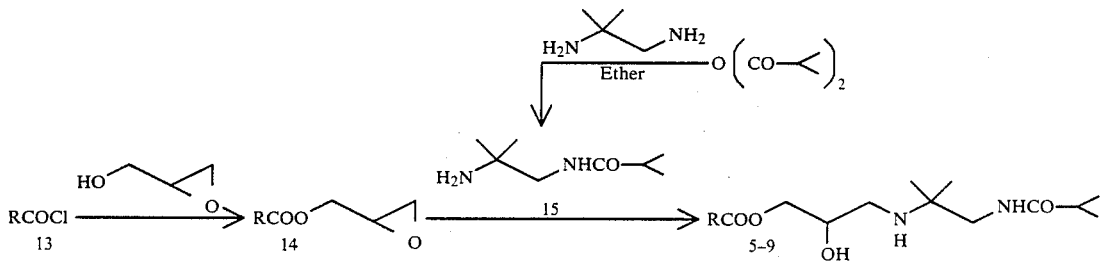

Preparation of Compound 14 (R=cyclopropyl)

To a cold solution (0° to 5° C.) of glycidol (7.4 g, 0.10 mole), triethylamine (12.0 g, 0.12 mole) in ether (400 ml) was added drop wise to cyclopropyl carboxylic acid chloride (10.5 g, 0.1 mole). The mixture was then stirred cedure described for the synthesis of compound 6, substituting cyclopropyl carboxylate with glycidol cinnamic ester and 1,1-dimethyl-2-[isopropylcarboxamido]ethylamine with 1,1-dimethyl-2[3-tetrahydrofuranylcarboxamide]ethylamine. Using the corresponding glycidolester and the aminoamides, compounds 5-9 were prepared using the above method. Typical procedure for the synthesis of compounds 10-11.

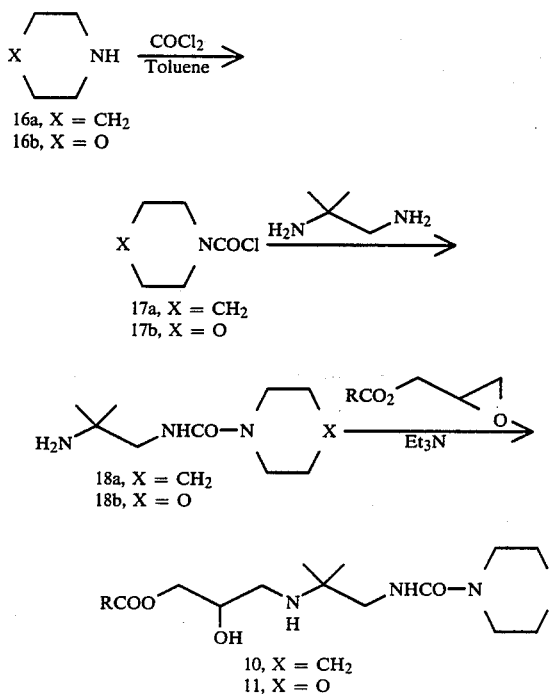

16a, X = CH$_2$
16b, X = O

17a, X = CH$_2$
17b, X = O

18a, X = CH$_2$
18b, X = O

10, X = CH$_2$
11, X = O

Preparation of Compound 18

Compound 17 was synthesized as described in the literature (Chem. Abstr. 47:12, 302f or 48:p5210d).

Compound 18b was synthesized by the method described for the preparation of compound 14 where the cyclopropylcarboxylic acid chloride is replaced with morpholine carbonylchloride 17b.

Compounds 10 and 11 were synthesized by the method described for the preparation of compound 6 where the aminoamide 15 is replaced with either intermediate 18a or 18b.

Beta-Blocking Activity in Vitro

Several of the compounds of the present invention were tested for β-blocking activity in vitro using guinea pig right atria and guinea pig tracheal strips mounted in a tissue bath containing oxygenated (95% O$_2$-5% CO$_2$) Krebs physiological salt solution at 37° C. Each tissue was suspended between a fixed glass rod and a Statham Universal Transducer connected to a Beckman recorder. Atria were allowed to beat spontaneously under a loading tension of approximately 0.5 gm. Intrinsic depressant or stimulant activity was determined for each compound by progressively increasing concentrations in the tissue baths at 60-minute intervals. Tissues were not washed between increments. The maximum concentration showing little or no cardiodepressant activity was chosen for blockade experiments. Changes in rate in response to isoproterenol, a standard β-receptor agonist, were measured in the absence and presence of test compounds. Spiral strips of guinea pig trachea were suspended under 5 gm resting tension and incubated with phentolamine, tropolone and cocaine. Active tension was generated by addition of carbachol ($3.0 \times 10^{-7}$M) and decreases in tension in response to isoproterenol were quantitated. Cumulative concentration-response curves were produced with isoproterenol both before and after 60-minute incubation of test compounds with atria and trachea. Compounds with β-blocking activity shifted concentration-response curves to the right. The blocking potency of test compounds was estimated by computing pA$_2$ values ($-\log K_8$) by the method of Furchgott, the Pharmacological Differentiation of Adrenergic Receptors, *Ann. N.Y. Acad. Sci.*, 139:553-570 (1967). Comparison of blockade of right atrial and tracheal responses to isoproterenol permits assessment of cardioselectivity of test compounds; i.e., cardioselective compounds are relatively more effective in blocking atrial rate than tracheal force response to isoproterenol. The degree of cardioselectivity was estimated from the ratio, kβ trachea/Kβ atria ($10^{(pA2atria - pA2trachea)}$). A ratio greater than one indicates cardioselectivity. Test drugs were dissolved in distilled water and added to the bath (30 mL) in a volume of 10 or 100 μL. The results of the in vitro tests are contained in Table 1. All of the test compounds are active β-blockers.

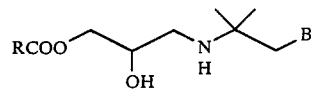

TABLE 1

| Compound No. | R | B | m.p. °C. | pA$_2$ |
|---|---|---|---|---|
| 1 | ⊲ | H | 160-67 | 6.0 |
| 5 | +  | NHCO-⊲ | 175-78 | 6.5 |
| 7 | ◇ | NHCO-⊲ | 130-33 | 6.5 |
| 8 | cyclopentenyl | NHCO-⊲ | 138-40 | 7.6 |

TABLE 1-continued

| Compound No. | R | B | m.p. °C. | pA$_2$ |
|---|---|---|---|---|
| 9 | cyclohexenylmethyl | NHCO—⟨ (isopropyl) | 110–11 | 6.9 |
| 6 | cyclopropyl | NHCO—⟨ | 102–05 | — |
| 11 | cyclopropyl | NHCO—N(morpholino) | 132–36 | 8.0 |
| 10 | cyclopropyl | NHCO—N(piperidino) | 136–38 | 8.1 |
| 2 | cyclopropyl | H | 140–42 | 6.5 |
| 3 | tert-butyl | H | 170–73 | 5.3 |
| 4 | cyclobutyl | H | 150–53 | 5.0 |
| 12 | styryl | NHCO—⟨tetrahydrofuranyl⟩ | 79(dec) | 7.3 |

What is claimed is:

1. A compound of the formula

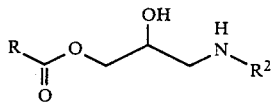

wherein R represents a straight or branched loweralkyl from 1 to about 6 carbon atoms, loweralkene from 2 to about 6 carbon atoms, or

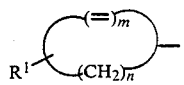

where m is o or 1 and n is 2, 3, 4, or 5 provided that when m is o, n is 2, 3, 4, or 5 and when m is 1, n is 3 or 4, and R$_1$ is hydrogen, a straight, branched or cyclic loweralkyl from 1 to about 6 carbon atoms or loweralkoxy, phenyl or substituted phenyl, and R$_2$ represents W-B wherein W represents alkylene of from 1 to about 10 carbon atoms which may be substituted with loweralkyl of from 1 to about 4 carbon atoms; and B represents —NHCONR$_3$R$_4$, wherein R$_3$ and R$_4$ together with N form a pyrrolidino, piperidino, piperazino, morpholino ring, or a pharmaceutically acceptable salt thereof.

2. A compound of the formula

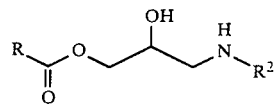

wherein R represents a straight or branched loweralkyl from 1 to about 6 carbon atoms, loweralkene from 2 to about 6 carbon atoms, cycloloweralkyl, cycloloweralkenyl or styryl and R$_2$ is W-B where W is 1,1-dimethylethylene and B is —NHCONR$_3$R$_4$ where R$_3$ and R$_4$ together with N form a morpholino or piperidino ring, or a pharmaceutically acceptable salt thereof.

3. A compound of claim 2 wherein R is propyl, butyl, cyclopropyl, cyclobutyl, cyclopentenyl, cyclohexenyl, or styryl, and R$_2$ is W-B where W is 1,1-dimethylethylene and B is —NHCONR$_3$R$_4$ where R$_3$ and R$_4$ together with N form a morpholino or piperidino ring.

4. A compound of claim 2 wherein R is cyclopropyl, and R$_2$ is W-B where W is 1,1-dimethylethylene and B is —NHCONR$_3$R$_4$ where R$_3$ and R$_4$ together with N form a morpholino ring.

5. A compound of claim 2 wherein R is cyclopropyl, and R$_2$ is W-B where W is 1,1-dimethylethylene and B is —NHCONR$_3$R$_4$ where R$_3$ and R$_4$ together with N form a piperidino ring.

6. A compound of the formula

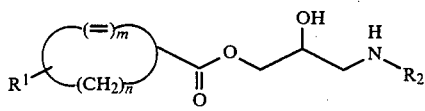

where m is o or 1 and n is 2, 3, 4, or 5 provided that when m is o, n is 2, 3, 4, or 5 and when m is 1, n is 3 or 4, and $R_1$ is hydrogen, a straight, branched or cyclic loweralkyl from 1 to about 6 carbon atoms or loweralkoxy, phenyl or substituted phenyl, and $R_2$ represents W-B wherein W represents alkylene of from 1 to about 10 carbon atoms which may be substituted with loweralkyl of from 1 to about 4 carbon atoms; and B represents —$NHCONR_3R_4$, wherein $R_3$ and $R_4$ together with N form a pyrrolidino, piperidino, piperazino, morpholino ring, or a pharmaceutically acceptable salt thereof.

7. A method of treating cardiac disorders in a patient comprising administering to a patient in need of such treatment a therapeutically effective amount of a compound of the formula.

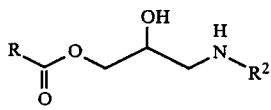

wherein R represents a straight or branched loweralkyl from 1 to about 6 carbon atoms, loweralkene from 2 to about 6 carbon atoms, or

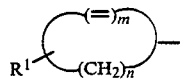

where m is o or 1 and n is 2, 3, 4, or 5 provided that when m is o, n is 2, 3, 4, or 5 and when m is 1, n is 3 or 4, and $R_1$ is hydrogen, a straight, branched or cyclic loweralkyl from 1 to about 6 carbon atoms or loweralkoxy, phenyl or substituted phenyl, and $R_2$ represents W-B wherein W represents alkylene of from 1 to about 10 carbon atoms which may be substituted with loweralkyl of from 1 to about 4 carbon atoms; and B represents —$NHCONR_3R_4$, wherein $R_3$ and $R_4$ together with N form a pyrrolidino, piperidino, piperazino, morpholino ring, or a pharmaceutically acceptable salt thereof.

8. The method of claim 7 wherein the compound is of the formula

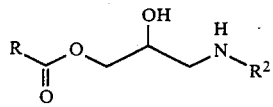

wherein R represents a straight or branched loweralkyl from 1 to about 6 carbon atoms, loweralkene from 2 to about 6 carbon atoms, cycloloweralkyl, or cycloloweralkenyl, and $R_2$ is W-B where W is 1,1-dimethylethylene and B is —$NHCONR_3R_4$ where $R_3$ and $R_4$ together with N form a morpholino or piperidino ring, or a pharmaceutically acceptable salt thereof.

9. The method of claim 8 wherein R is propyl, butyl, cyclopropyl, cyclobutyl, cyclopentenyl, or cyclohexenyl, styryl, and $R_2$ is W-B where W is 1,1-dimethylethylene and B is —$NHCONR_3R_4$ where $R_3$ and $R_4$ together with N form a morpholino or piperidino ring.

10. The method of claim 7 wherein the compound is of the formula

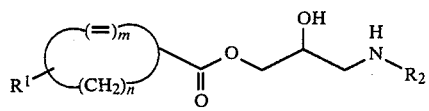

where m is o or 1 and n is 2, 3, 4, or 5 provided that when m is o, n is 2, 3, 4, or 5 and when m is 1, n is 3 or 4, and $R_1$ is hydrogen, a straight, branched or cyclic loweralkyl from 1 to about 6 carbon atoms or loweralkoxy, phenyl or substituted phenyl, and $R_2$ represents W-B wherein W represents alkylene of from 1 to about 10 carbon atoms which may be substituted with loweralkyl of from 1 to about 4 carbon atoms; and B represents —$NHCONR_3R_4$, wherein $R_3$ and $R_4$ together with N form a pyrrolidino, piperidino, piperazino, morpholino ring, or a pharmaceutically acceptable salt thereof.

11. A pharmaceutical composition for treating cardiac conditions which composition contains an effective amount for treating such conditions of a compound having beta-adrenergic blocking activity of the formula

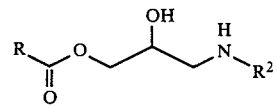

wherein R represents a straight or branched loweralkyl from 1 to about 6 carbon atoms, loweralkene from 2 to about 6 carbon atoms, or

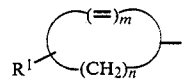

where m is o or 1 and n is 2, 3, 4, or 5 provided that when m is o, n is 2, 3, 4, or 5 and when m is 1, n is 3 or 4, and $R_1$ is hydrogen, a straight, branched or cyclic loweralkyl from 1 to about 6 carbon atoms or loweralkoxy, phenyl or substituted phenyl, and $R_2$ represents W-B wherein W represents alkylene of from 1 to about 10 carbon atoms which may be substituted with loweralkyl of from 1 to about 4 carbon atoms; and B represents —$NHCONR_3R_4$, wherein $R_3$ and $R_4$ together with N form a pyrrolidino, piperidino, piperazino, morpholino ring, or a pharmaceutically acceptable salt thereof, in admixture with a pharmaceutically acceptable carrier or diluent.

12. The composition of claim 11 wherein the compound is of the formula

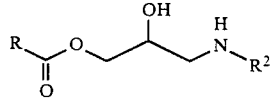

wherein R represents a straight or branched loweralkyl from 1 to about 6 carbon atoms, loweralkene from 2 to about 6 carbon atoms, cycloloweralkyl, or cycloloweralkenyl, and $R_2$ is W-B where W is 1,1-dimethylethylene and B is —NHCONR$_3$R$_4$ where R$_3$ and R$_4$ together with N form a morpholino or piperidino ring, or a pharmaceutically accepatalbe salt thereof.

13. The composition of claim 11 wherein the compound is of the formula

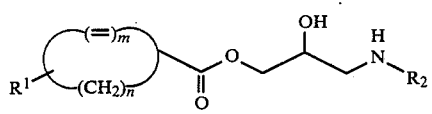

where m is o and 1 and n is 2, 3, 4 or 5 provided that when m is o, n is 2, 3, 4, or 5 and when m is 1, n is 3 or 4, and R$_1$ is hydrogen, a straight, branched or cyclic loweralkyl from 1 to about 6 carbon atoms or loweralkoxy, phenyl or substituted phenyl, and R$_2$ represents W-B wherein W represents alkylene of from 1 to about 10 carbon atoms which may be substituted with loweralkyl of from 1 to about 4 carbon atoms; and B represents —NHCONR$_3$R$_4$, wherein R$_3$ and R$_4$ together with N form a pyrrolidino, piperidino, piperazino, morpholino ring, or a pharmaceutically acceptable salt thereof.

* * * * *